United States Patent [19]

Meisel et al.

[11] Patent Number: 5,840,902
[45] Date of Patent: *Nov. 24, 1998

[54] PROCESS FOR THE PREPARATION OF BETA-HYDROXYALKYPICOLINIUM SALTS

[75] Inventors: Karlheinrich Meisel, Odenthal; Klaus Walz, Leverkusen; Gerd-Friedrich Renner, Kürten; Hans Schulze, Köln; Carsten Gerdes, Leverkusen; Karl-Rudolf Gassen, Ratingen; Reiner Ditzer, Odenthal; Lothar Klein, Leverkusen, all of Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 752,885

[22] Filed: Nov. 20, 1996

[30] Foreign Application Priority Data

Nov. 28, 1995 [DE] Germany .................. 195 44 268.7

[51] Int. Cl.$^6$ .............. C07D 221/04; C07D 213/127; C07D 213/26; C07D 215/10
[52] U.S. Cl. .................. 546/79; 546/182; 546/329; 546/330; 546/334; 546/335
[58] Field of Search ............... 546/344, 329, 546/320, 334, 335, 79, 182

[56] References Cited

U.S. PATENT DOCUMENTS

| | | | |
|---|---|---|---|
| 3,895,933 | 7/1975 | Jäger et al. | 71/94 |
| 4,754,021 | 6/1988 | Möckli | 534/605 |
| 4,847,364 | 7/1989 | Möchli | 534/605 |
| 4,883,866 | 11/1989 | Möchli | 534/606 |
| 5,256,784 | 10/1993 | Francis et al. | 544/294 |

FOREIGN PATENT DOCUMENTS

| | | |
|---|---|---|
| 0176472 | 4/1986 | European Pat. Off. . |
| 2230179 | 1/1974 | Germany . |

OTHER PUBLICATIONS

Chem. Heterocycl. Comp. (Eng. Transl.), Bd. 26, Nr. 4, Apr. 1990, Seiten 507–510, XP000652651, Garkusha–Bozhko, V.S., et al.: "Reaction of Pyridines with Epichlorohydrin", * pp. 435–437, die Beispiele*, (original article Jun. 10, 1988).

J. Am. Chem. Soc., Bd., 71, 1949, Washington, Seiten 3498–3500, XP000652725, King, L.C., et al.: "Reactions of 1,2–Expoxides with Salts of Organic Bases. I. Styrene Oxide", * p. 3499, Table I *.

Chem. Heterocycl. Comp. (Eng. Transl.), Bd. 10, Oct. 1984, pp. 1162–1166, XP000652652, Shishkin, G.V.: "Diazabicycloalkanes with nitrogen atoms . . . " (original article Mar. 29, 1984).

*Primary Examiner*—Alan L. Rotman
*Attorney, Agent, or Firm*—Sprung Kramer Schaefer & Briscoe

[57] ABSTRACT

β-Hydroxyalkylpicolinium salts of the formula (I)

$$\text{(I)}$$

wherein A, $R^1$ to $R^3$ and X have the meanings given in the description, which are obtained by reaction of picolines of the formula (II)

$$\text{(II)}$$

with alkylene oxides of the formula (III) in the presence of a 1- to 3-basic acid and in water or an organic solvent as the reaction medium and are used as intermediate products for the preparation of cationic dyestuffs, and dyestuff preparations comprising such cationic dyestuffs.

18 Claims, No Drawings

PROCESS FOR THE PREPARATION OF BETA-HYDROXYALKYPICOLINIUM SALTS

The invention relates to β-hydroxyalkylpicolinium salts, a process for their preparation, their use as intermediate products for the preparation of cationic dyestuffs, and dyestuff preparations of cationic dyestuffs prepared therefrom having a low chloride content.

Hydroxyethylpicoliniun salts are important intermediate products for the preparation of cationic dyestuffs, in particular in the form of their chlorides, which are known, for example, from EP-A 176 472. The chlorides are in general obtained by reaction of chloroethanol with picolines. However, chloroethanol, which presents problems because it is toxic and corrosive, is used in this process.

The object of the present invention was to provide a process for the preparation of hydroxyethylpicolinium salts which does not have the disadvantages mentioned.

A process has now been found for the preparation of β-hydroxyalkylpicolinium salts of the formula (I)

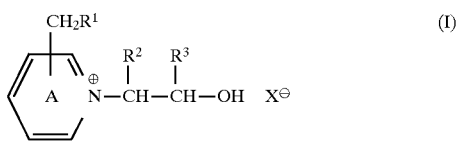

wherein the ring A optionally carries further substituents and/or can be fused with carbo- or heterocyclic rings, preferably aromatic rings, $R^1$ represents H, cyano, $C_1$–$C_4$-alkoxycarbonyl or optionally substituted $C_1$–$C_4$-alkyl, in particular $C_1$–$C_2$-alkyl, $R^2$ and $R^3$ independently of one another denote H, optionally substituted $C_1$–$C_4$-alkyl, in particular $C_1$–$C_2$-alkyl, or optionally substituted phenyl and $X^\ominus$ represents the radical of one equivalent of a 1- to 3-basic acid, which is characterized in that picolines of the formula (II)

wherein $R^1$ has the abovementioned meaning and the ring A can be further substituted in the manner described above, are reacted with alkylene oxides of the formula (III)

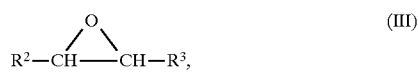

wherein $R^2$ and $R^3$ have the abovementioned meaning, in the presence of a 1- to 3-basic acid.

Suitable substituents which may be mentioned for the $C_1$–$C_4$-alkyl radicals in the meaning of $R^2$ and $R^3$ are, for example, CN, aryloxy, such as phenoxy, or $C_1$–$C_4$-alkoxycarbonyls.

Suitable substituents which may be mentioned for phenyl radicals are, for example, $C_1$–$C_4$-alkyl, halogen, in particular Cl, Br and F, CN, $NO_2$ or $C_1$–$C_2$-alkylsulphonyl.

In a particularly preferred embodiment of the process according to the invention, alkylene oxides of the formula (III) which are employed are ethylene oxide, propylene oxide, 1,2- or 2,3-butylene oxide, styrene oxide or

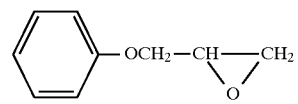

Ethylene oxide and propylene oxide are especially preferred, in particular ethylene oxide.

Preferred picolines of the formula (II) which may be mentioned are: 4-methylpyridine, 2-methylpyridine, 4-methylquinoline, 2-methylquinoline or 4-methyltetrahydroquinoline. 4-Methylpyridine is particularly preferred.

Examples which may be mentioned of suitable further substituents of the ring A are: nitro, halogen, cyano, $C_1$–$C_4$-alkyl, $C_1$–$C_4$-alkoxy, acetylamino or dimethylamino. In the case where the ring A is fused with other rings, these are preferably carbocyclic, in particular aromatic benzo or naphthalene rings. These are particularly preferably fused on in the 2,3-position of the A ring.

The reaction medium used is preferably water or a mixture of water and a polar organic solvent, the polar organic solvent preferably being miscible with water, and in particular soluble in water. Particularly preferred organic solvents which may be mentioned are glycols, such as ethylene glycol, diethylene glycol, 1,2- and 1,3-propanediol, glycerol and pentaerythritol, glycol ethers, such as n-butyl-diethylene glycol, methoxypropanol and dimethylformamide. Ethylene glycol or 1,2-propylene glycol is especially preferred.

The mixing ratio of water to organic polar solvent can be varied over wide ranges. A weight ratio of 1:3 to 1:10 has proved advantageous.

A suitable 1- to 3-basic acid which may be mentioned is either an inorganic acid, such as, for example, HCl, $H_2SO_4$, $H_3PO_4$, $HNO_3$, HBr, HI or $H_2CO_3$, or an organic carboxylic, sulphonic or sulphinic acid, such as, for example, a $C_1$–$C_6$-mono- or -dicarboxylic acid, such as formic acid, acetic acid or oxalic acid, hydroxy-$C_1$–$C_4$-alkylsulphonic acids or mixtures thereof.

The acid can be added in the pure form or in concentrated or dilute aqueous solution. Mixtures of acids are also possible. $H_2SO_4$, in particular concentrated $H_2SO_4$ (48 to 98% strength by weight), is particularly preferred.

The anion $X^\ominus$ of the hydroxyethylpicolinium salt is derived from the 1- to 3-basic acid. Thus, for example, β-hydroxyethyl-sulphate, as an anion, is also a derivative, understood in the context of this Application, of the 2-basic acid $H_2SO_4$, which is formed when ethylene oxide is used as the alkylene oxide.

The process according to the invention is as a rule carried out at a temperature from 0° to 160° C., in particular at 70° to 100° C. The process according to the invention can be carried out under normal pressure or reduced or increased pressure. It is advantageous to carry out the reaction under normal pressure or under increased pressure, in particular under 3 to 6 bar. An increase in the pressure is advantageous, in particular, if the alkylene oxide component of the formula (III) is present in gaseous form at the reaction temperature. This can have an advantageous effect, in particular with ethylene oxide or propylene oxide.

The process according to the invention is preferably carried out such that the molar ratio of the 1- to 3-basic acid to alkylene oxide of the formula (II) is 1:1 to 1:2. The molar ratio of alkylene oxide to picoline of the formula (I) employed is preferably 1:1 to 2:1. The reaction can of course also be carried out with other ratios, but such ratios do not lead to an unexpected advantage. In a preferred process variant, the picoline of the formula (II) is initially introduced into the reaction vessel in water or in a mixture of water and a polar organic solvent as the reaction medium, and the alkylene oxide component and acid component are added, preferably separately. In a preferred embodiment, acid is added to form the picolinium salt in an amount such that a pH of 2 to 8, preferably 4 to 7, is established in the reaction medium.

It is furthermore advantageous to control the addition of acid and alkylene oxide such that the pH of the reaction mixture during the reaction remains in the pH range mentioned. The alkylene oxide can be added as a function of the addition of acid such that the pH is kept in the range from 2 to 8, preferably from 4 to 7.

Particularly preferably, however, the acid is added as a function of the addition of the alkylene oxide (III), the advantageous pH ranges being maintained as described above. The pH can be determined during the reaction with pH paper or, preferably, with a commercially available pH electrode. The use of a pH electrode has the advantage that it can be used, in connection with a suitable control unit, directly with an addition device which controls the addition of one of the two components as a function of the desired pH, as described above. The process according to the invention is particularly preferably carried out in a $CO_2$ atmosphere. This leads to compounds of the formula (I) which have a particularly high purity, especially if non-volatile 1- to 3-basic acids, such as $H_2SO_4$, are used.

The salts obtained by the process according to the invention can be isolated from the reaction mixture, for example, by removal of the reaction medium used by distillation.

The process according to the invention where no halogen-containing 1- to 3-basic acids are used is particularly preferred.

The invention furthermore relates to new β-hydroxyalkylpicolinium salts of the formula (I), wherein $R^1$ to $R^3$ have the abovementioned meanings and $X^\ominus$ represents a radical of one equivalent of a 1- to 3-basic acid, apart from halide. These are called compounds of the formula (Ia) below. Particularly preferred β-hydroxyalkylpicolinium salts of the formula (Ia) are those wherein $X^\ominus$ denotes the radical of one equivalent of $H_2SO_4$.

Surprisingly, the β-hydroxyalkylpicolinium salts according to the invention have a significantly lower corrosiveness than the corresponding chlorides which are known, for example, from EP-A 176 472.

The invention furthermore relates to a process for the preparation of cationic dyestuffs, which is characterized in that the β-hydroxyalkylpicolinium salts (Ia) or the β-hydroxyalkylpicolinium salts (I) obtained by the above process are reacted with aromatic or heterocyclic aldehydes. This process where the β-hydroxyalkylpicolinium salts obtained by the above process are not intermediately isolated is especially preferred.

Examples which may be mentioned of aromatic or heterocyclic aldehydes which are particularly suitable for this purpose are: optionally substituted benzaldehydes, such as, for example, 4-dimethylaminobenzaldehyde, 4-diethylaminobenzaldehyde, 4-methylbenzylaminobenzaldehyde, 4-ethylbenzylaminobenzaldehyde, 4-ethyl-hydroxyethylaminobenzaldehyde, 4-ethyl-β-chloroethylaminobenzaldehyde, 1-methyl-β-chloroethylaminobenzaldehyde, 4-dicyanoethylaminobenzaldehyde and 4-ethylcyanoethylaminobenzaldehyde, and $C_1$- to $C_4$-alkoxybenzaldehydes, which can optionally be further substituted, such as, for example, 4-methoxybenzaldehyde, 2,4-dimethoxybenzaldehyde, 3,4-dimethoxybenzaldehyde and 4-β-methoxyethoxy-benzaldehyde, and heterocyclic aldehydes, such as, for example, carbazole-aldehyde, indole-3-aldehyde, 2-methyl-3-formylindole, 1,2-dimethyl-3-formylindole, 1-methyl-2-phenyl-3-formylindole, 1-benzyl-2-phenyl-3-formylindole, 1,2-dimethyl-5-methoxy-3-formylindole, 1,2-dimethyl-5-chloro-3-formylindole, 1,2-dimethyl-5-methyl-3-formylindole, 1,2-dimethyl-5,6-dichloro-3-formylindole, 1-methyl-2-phenyl-5-methoxy-3-formylindole, 1-methyl-2-phenyl-5-chloro-3-formylindole, 1-methyl-2-phenyl-5-methyl-3-formylindole, 1-methyl-2-phenyl-5,6-dichloro-3-formylindole and 2,2,4-trimethyl-6-formyltetrahydroquinoline.

It has furthermore been found that dyestuff preparations having a chloride content of less than 0.5% by weight, preferably less than 0.1% by weight, based on the dyestuff preparation, which comprise at least one cationic dyestuff which has been prepared from a β-hydroxyalkylpicolinium salt (Ia) according to the invention have significantly lower corrosive properties. This applies to solid preparations, that is to say powders or granules, and in particular to liquid, especially aqueous, preparations.

The dyestuff preparations according to the invention which are essentially free from chloride ions, in particular halide ions, are particularly preferred.

Preferred possible cationic dyestuffs of these dyestuff preparations are those which have been prepared from β-hydroxyalkylpicolinium salts (Ia) by the process according to the invention. Those which furthermore comprise the sulphuric acid half-esters β-hydroxyalkyl-hydrogensulphates, in particular β-hydroxyethyl-hydrogensulphate, in addition to these cationic dyestuffs are especially preferred.

The solid dyestuff preparations according to the invention in general comprise
a) 50 to 80% by weight of at least one cationic dyestuff prepared from a β-hydroxyalkylpicolinium salt (Ia)
b) 0 to 0.5% by weight of $Cl^\ominus$ Remainder standardizing agents, residual moisture and other customary additives.

The liquid dyestuff preparations according to the invention in general comprise
a) 20 to 50% by weight of at least one cationic dyestuff prepared from a β-hydroxyalkylpicolinium salt (Ia)
b) 0 to 0.5% by weight of $Cl^\ominus$
c) 0 to 30, in particular 5 to 25% by weight of an organic acid, in particular acetic acid,
and if appropriate further additives customary for aqueous preparations of cationic dyestuffs.

Further advantageous additives which may be mentioned are those designated d) to f) below, which give advantageous dyestuff preparations in the amounts ranges stated:
d) 0 to 30% by weight of β-hydroxyalkyl-hydrogensulphate, in particular β-hydroxyethyl-hydrogensulphate,
e) 0 to 15% by weight of ethylene glycol,
f) 0 to 15% by weight of propylene glycol.

The invention furthermore relates to dyestuff preparations having a chloride content of less than 0.5% by weight, in particular less than 0.1% by weight, based on the dyestuff preparations, which comprise a cationic dyestuff and β-hydroxyalkyl-hydrogensulphate, in particular β-hydroxyethyl-hydrogensulphate.

Preferred cationic dyestuffs which are prepared using the β-hydroxyalkylpicolinium salts of the formula (I) prepared by the process according to the invention, and those which are preferably contained in the dyestuff preparations according to the invention correspond to the formula (IV)

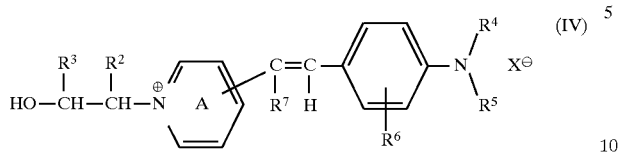

wherein $R^2$, $R^3$, A and $X^\ominus$ have the abovementioned meaning and $R^4$ and $R^5$ independently of one another denote $C_1$–$C_4$-alkyl or phenyl, which are optionally substituted by phenyl, 4-chlorophenyl, 4-cyanophenyl or by one or two substituents from the group consisting of OH, $C_1$–$C_4$-alkoxy, halogen and cyano, $R^6$ denotes H, halogen, CN, nitro or $C_2$–$C_4$-alkyl and $R^7$ denotes H or CN.

Preferred cationic dyestuffs of the formula IV are those which correspond to one of the following formulae.

| Structure | | $\lambda_{max}$ |
|---|---|---|
| HO—H$_2$C—H$_2$C—N$^\oplus$(pyridyl)—CH=CH—(phenyl)—N(CH$_3$)(CH$_2$-phenyl) | X$^-$ | 480 nm |
| HO—CH$_2$—CH$_2$—N$^\oplus$(pyridyl)—CH=CH—(phenyl)—N(C$_2$H$_5$)(CH$_2$-phenyl) | X$^-$ | 481 nm |
| HO—CH$_2$—CH$_2$—N$^\oplus$(pyridyl)—CH=CH—(phenyl)—N(C$_2$H$_5$)(C$_2$H$_4$—CN) | X$^-$ | 488 nm |
| HO—CH$_2$—CH$_2$—N$^\oplus$(pyridyl)—CH=CH—(phenyl)—N(C$_2$H$_4$CN)(C$_2$H$_4$CN) | X$^-$ | 502 nm |
| HO—CH$_2$—CH$_2$—N$^\oplus$(pyridyl)—CH=CH—(phenyl)—N(C$_2$H$_4$OH)(C$_2$H$_4$OH) | X$^-$ | 486 nm |
| HO—CH$_2$—CH$_2$—N$^\oplus$(pyridyl)—CH=CH—(phenyl)—N(C$_2$H$_4$CN)(CH$_2$-phenyl) | X$^-$ | 490 nm |
| HO—CH$_2$—CH$_2$—N$^\oplus$(pyridyl)—CH=CH—(phenyl)—N(C$_2$H$_4$OH)(CH$_2$-phenyl) | X$^-$ | 483 nm |
| HO—CH$_2$—CH$_2$—N$^\oplus$(pyridyl)—CH=CH—(phenyl)—N(CH$_3$)(CH$_2$—CH$_2$-phenyl) | X$^-$ | 478 nm |
| HO—C(CH$_3$)—CH$_2$—N$^\oplus$(pyridyl)—CH=CH—(phenyl)—N(CH$_3$)(CH$_2$-phenyl) | X$^-$ | 480 nm |

-continued

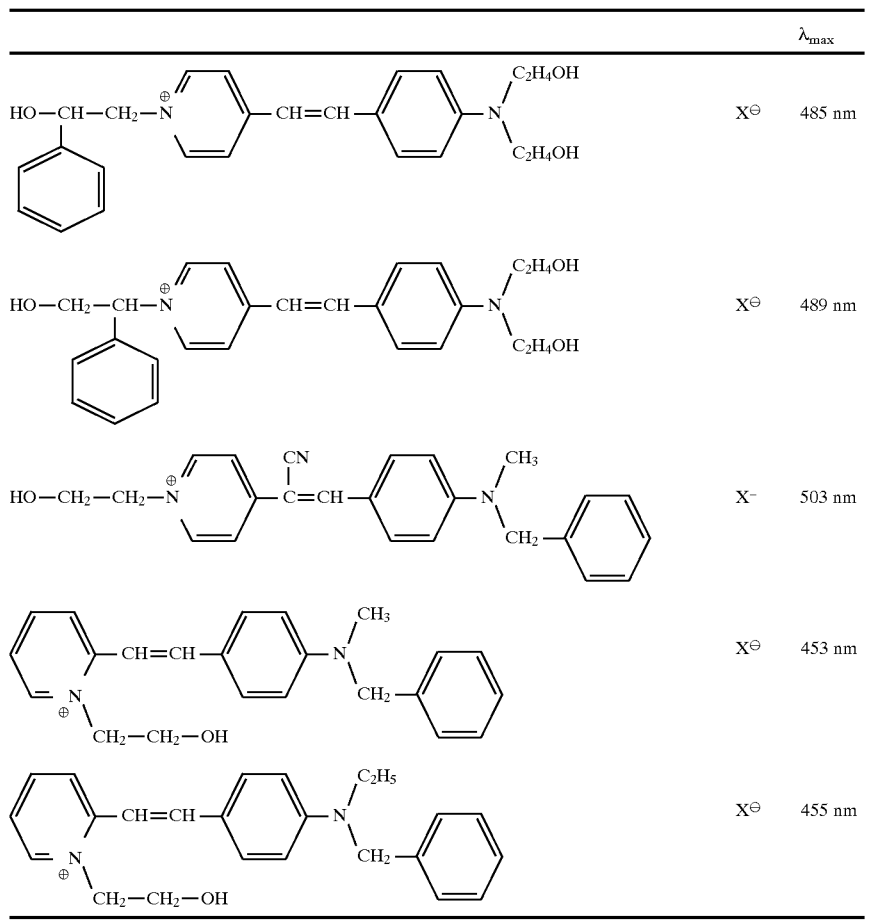

The aminostyryl radical is particularly preferably in the ortho- or para-position, in particular in the para-position, relative to the ring nitrogen atom of the picolinium radical.

EXAMPLE

Example 1

Apparatus

Vessel with a ground glass flange with a bottom outlet valve, distillation attachment and connection for metering in $CO_2$, ethylene oxide and sulphuric acid, addition of which is regulated via a titrator.

Process 480 g of 4-methylpyridine, 316.5 g of 1,2-propanediol and 77.4 g of water were initially introduced into the vessel under a $CO_2$ atmosphere. A pH of 5 was established in this mixture with concentrated sulphuric acid. The batch was heated to 80° C. Ethylene oxide was passed into this apparatus at pH 5, while simultaneously metering in sulphuric acid with the aid of a titrator, until a sulphuric acid consumption of 300 g of sulphuric acid was reached. The pH was allowed to rise to 6 and further ethylene oxide was then passed in at this pH until a further 50 g of sulphuric acid had been consumed. The ethylene oxide stream was stopped. By reaction of the dissolved ethylene oxide, another 7 g of sulphuric acid were consumed during subsequent stirring. The total sulphuric acid consumption was 357 g. The metering in of sulphuric acid was stopped and the batch was cooled to room temperature and drained off. Yield: 1518 g of a reaction mixture of the following composition: picolinium salt 45.6% (based on a molecular weight of 138.2), corresponds to 97% of theory, 4-methylpyridine 1.8%, by-product 1.3%, remainder water and 1,2-propanediol, β-hydroxyethyl-halogenosulphate and the like.

Example 2

The process was carried out analogously to Example 1, but instead of sulphuric acid, 540 g of concentrated acetic acid were employed. 1810 g of a pale yellow product mixture of the following composition were obtained:

1.2% of 4-methylpyridine 53.5% of β-hydroxyethylpicolinium acetate

1% of by-product

Remainder: water, propanediol, ethylene glycol acid, acetic acid ethylene glycol ester

Example 3

742 parts of γ-picoline, 119 parts of water and 489 parts of propylene glycol are initially introduced into a stirred vessel and 199 parts of 98% strength sulphuric acid are then added, while cooling, such that the temperature rises to 60° to 70° C. The reaction vessel is then flushed with nitrogen, to remove atmospheric oxygen, and heated to 80° C. 125 parts of ethylene oxide are then added at 80° to 90° C. in the course of about 1 hour. During this operation, the pH of the reaction mixture should not rise above 7. After addition of a further 200 parts of sulphuric acid, a further 186 parts of ethylene oxide are added in the course of about 1 hour, until the pH of the reaction mixture has reached 7.5 to 8. The mixture is subsequently stirred for a further ½ hour and then distilled under a vacuum of 20 mbar at 90° C. until no further distillate passes over. A liquid product which, in addition to about 30% of propylene oxide, comprises about 43% of hydroxyethylpicolinium sulphate mixed with 29% of hydroxyethylpicolinium hydroxyethyl-sulphate is obtained. (Content of hydroxyethylpicolinium cation: 45 to 50%, determination by HPLC)

Example 4

The process was carried out analogously to Example 1, but instead of sulphuric acid, 357 g of phosphoric acid were employed. 1545 g of a product mixture of the following composition are obtained: picolinium salt: 43.6%, 4-methylpyridine: 1.7%, by-product: 1.4%, remainder water, propanediol, ethylene glycol and phosphoric acid mono- and diglycol ester.

Example 5

From the reaction mixture from Example 1, 124.4 g of a mixture of water and 1,2-propanediol are distilled off under a waterpump vacuum up to a bath temperature of 100° C. The mixture is allowed to cool to 60° C. and 957.7 g of 4-ethylbenzylaminobenzaldehyde and 50 ml of piperidine are added at this temperature. The mixture is then heated to 80° C. and subsequently stirred at this temperature for 7 hours. The following morning it is distilled under a waterpump vacuum for 4 hours. 2467.7 g of non-formulated dyestuff are obtained. The tinctorial strength is adjusted by addition of 730 g of glacial acetic acid and 1459 g of water.

Yield: 4656 g of liquid formulation

Example 6

A cationic dyestuff prepared analogously to Example 5, for the preparation of which, however, hydroxyethylpicolinium chloride was used, was employed in the form of its aqueous dyestuff preparation in a corrosion test in which it was to be tested whether V2A or V4A steel materials corrode in the presence of this dyestuff.

The results of the current density/potential measurements showed that the materials tested corroded.

Example 7

Analogously to Example 6, the materials were tested for corrosion in the presence of an aqueous dyestuff preparation of the chloride-free dyestuff from Example 5. The results of the current density/potential measurements showed that the V2A and V4A steel materials tested did not corrode.

We claim:
1. Process for the preparation of a β-hydroxyalkylpicolinium salt of the formula (I)

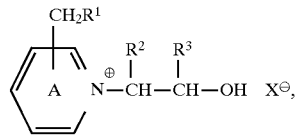

wherein the ring A is unsubstituted or carries further substituents selected from the group consisting of nitro, halogen, cyano, $C_1$–$C_4$-alkyl, $C_1$–$C_4$-alkoxy, acetylamino or dimethylamino and/or is fused with aromatic benzo or naphthalene rings, $R^1$ represents H, cyano, $C_1$–$C_4$-alkoxycarbonyl or $C_1$–$C_4$-alkyl, $R^2$ and $R^3$ independently of one another denote H, unsubstituted or substituted $C_1$–$C_4$-alkyl or unsubstituted or substituted phenyl wherein the substituents for $C_1$–$C_4$-alkyl are selected from the group consisting of CN, aryloxy and $C_1$–$C_4$ alkoxycarbonyls and the substituents for phenyl are selected from the group consisting of $C_1$–$C_4$-alkyl, halogen, CN, $NO_2$ and $C_1$–$C_2$-alkylsulphonyl, and $X^\ominus$ represents the radical of one equivalent of a 1- to 3-basic acid, wherein a picoline of the formula (II)

wherein A and $R^1$ have the abovementioned meanings, is reacted with an alkylene oxide of the formula (III)

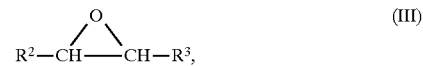

wherein $R^2$ and $R^3$ have the abovementioned meaning, in the presence of a 1- to 3-basic acid and in a reaction medium of water or a mixture of water and a polar solvent, at a temperature of 0°–160° C. and a pH of 2–8.

2. The process according to claim 1, wherein ethylene oxide, propylene oxide, 1,2- or 2,3-butylene oxide, styrene oxide or

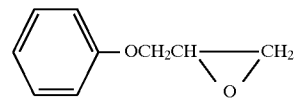

is employed as alkylene oxide of the formula (III).

3. Process according to claim 1 wherein ethylene oxide is employed as alkylene oxide.

4. The process according to claim 1, wherein 4-methylpyridine or 2-methylpyridine, is employed as picoline of the formula (II).

5. The process according to claim 1, wherein HCl, $H_2SO_4$, $H_3PO_4$, $HNO_3$, HBr, HI, $H_2CO_3$ or an organic carboxylic, sulphonic or sulphinic acid, is employed as the 1- to 3-basic acid.

6. The process according to claim 1, wherein the 1- to 3-basic acid and the alkylene oxide of the formula (III) are added to the picoline.

7. The process according to claim 1, wherein the reaction is carried out at a pH of 2 to 8.

8. The process according to claim 1, wherein the reaction is carried out in a $CO_2$ atmosphere.

9. The process according to claim 1, wherein 4-methylpyridine is employed a picoline of the formula II.

10. The process according to claim 1, wherein $H_2SO_4$ is employed as the 1- to 3-basic acid.

11. The process according to claim 1, wherein the reaction is carried out at a pH of 4 to 7.

12. A β-Hydroxyalkylpicolinium salt of the formula (Ia)

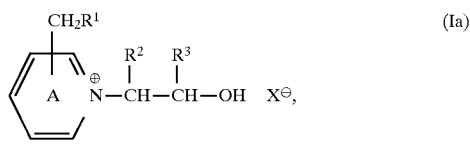

wherein
the ring A is unsubstituted or carries further substituents and/or is fused with carbo- or heterocyclic rings,
- $R^1$ represents H, cyano, $C_1$–$C_4$-alkoxycarbonyl or unsubstituted or substituted $C_1$–$C_4$-alkyl,
- $R^2$ and $R^3$ independently of one another denote H, unsubstituted or substituted $C_1$–$C_4$-alkyl or unsubstituted or substituted phenyl and
- $X^\ominus$ represents the radical of one equivalent of a 1- to 3-basic acid, excluding halide.

13. A process for the preparation of cationic dyestuffs, wherein the β-hydroxyalkylpicolinium salt obtained according to claim 1 is reacted with an aromatic aldehyde.

14. A dyestuff preparation having a chloride content of less than 0.5% by weight, based on the dyestuff preparation, which comprises at least one cationic dyestuff which has been prepared from the β-hydroxyalkylpicolinium salt according to claim 12.

15. The dyestuff preparation according to claim 14, further comprising β-hydroxyethyl-hydrogensulphate.

16. A dyestuff preparation having a chloride content of less than 0.5% by weight, based on the total weight of the preparation and which comprises a cationic dyestuff and a β-hydroxyalkyl-hydrogensulphate.

17. A process for the preparation of cationic dyestuffs, wherein the β-hydroxyalkylpicolinium salt obtained according to claim 8 is reacted with an aromatic aldehyde.

18. A dyestuff preparation having a chloride content of less than 0.5% by weight, based on the dyestuff preparation, which comprises at least one cationic dyestuff which has been prepared from the β-hydroxyalkylpicolinium salt obtained by the process of claim 1.

* * * * *

UNITED STATES PATENT AND TRADEMARK OFFICE
CERTIFICATE OF CORRECTION

PATENT NO. : 5,840,902
DATED      : November 24, 1998
INVENTOR(S): Meisel, et al.

It is certified that error appears in the above-identified patent and that said Letters Patent is hereby corrected as shown below:

| | |
|---|---|
| Title Page & Col. 1 line 2 | [54] Title: Line 2 delete " HYDROXY-ALKYPICOLINIUM " and substitute -- HYDROXYALKYLPICOLINIUM -- |
| Title Page | U.S. PATENT DOCUMENTS: After " 7/1989" and " 11/1989 " delete " Mochli " and substitute -- Mockli -- |

Signed and Sealed this

Sixth Day of July, 1999

Attest:

Q. TODD DICKINSON

Attesting Officer

Acting Commissioner of Patents and Trademarks